(12) United States Patent
Chung et al.

(10) Patent No.: US 11,771,636 B2
(45) Date of Patent: Oct. 3, 2023

(54) COMPOSITION FOR PROMOTING HAIR GROWTH COMPRISING ADIPONECTIN-DERIVED PEPTIDE

(71) Applicant: JUNGJINHO EFFECT INC., Seoul (KR)

(72) Inventors: Jin Ho Chung, Seoul (KR); Oh Sang Kwon, Seoul (KR); Eun Ju Kim, Seoul (KR); Jin Yong Kim, Seoul (KR); Dong Hun Lee, Seoul (KR)

(73) Assignee: JUNGJINHO EFFECT INC., Seoul (KR)

( * ) Notice: Subject to any disclaimer, the term of this patent is extended or adjusted under 35 U.S.C. 154(b) by 84 days.

(21) Appl. No.: 17/272,914

(22) PCT Filed: Sep. 3, 2018

(86) PCT No.: PCT/KR2018/010236
§ 371 (c)(1),
(2) Date: Mar. 2, 2021

(87) PCT Pub. No.: WO2020/050428
PCT Pub. Date: Mar. 12, 2020

(65) Prior Publication Data
US 2021/0196610 A1    Jul. 1, 2021

(51) Int. Cl.
*A61K 8/64* (2006.01)
*A61Q 7/00* (2006.01)

(52) U.S. Cl.
CPC . *A61K 8/64* (2013.01); *A61Q 7/00* (2013.01)

(58) Field of Classification Search
CPC .................................................... A61Q 7/00
See application file for complete search history.

(56) References Cited

U.S. PATENT DOCUMENTS

| | | | |
|---|---|---|---|
| 2014/0057833 A1 | 2/2014 | Otvos et al. | |
| 2016/0222077 A1 | 8/2016 | Hahn et al. | |

FOREIGN PATENT DOCUMENTS

| | | |
|---|---|---|
| KR | 20130083103 A | 7/2013 |
| KR | 20140089505 A | 7/2014 |
| KR | 20150032401 A | 3/2015 |
| KR | 20160021086 A | 2/2016 |
| KR | 20160070508 A | 6/2016 |
| KR | 20180100945 A | 9/2018 |
| TW | 201717992 A * | 6/2017 |
| WO | 2008/035527 A1 | 3/2008 |

OTHER PUBLICATIONS

International Search Report and Written Opinion from International Patent Application No. PCT/KR2018/010236, dated May 27, 2019, 14 pages.
Lbbers et al., "Adiponectin in mice with altered GH action: links to insulin sensitivity and longevity?", Journal of Endocrinology, 2013, pp. 363-374, vol. 216, No. 3, Bioscientifica Ltd., Great Britain.
Otvos et al., "Design and development of a peptide-based adiponectin receptor agonist for cancer treatment", BMC Biotechnology, 2011, pp. 1-14, vol. 11, No. 90.
Otvos et al., "Development of second generation peptides modulating cellular adiponectin receptor responses", Frontiers in Chemistry, 2014, pp. 1-15, vol. 2, No. 93.
Won et al, "Hair Growth-Promoting Effects of Adiponectin In Vitro", Journal of Investigative Dermatology, 2012, pp. 2849-2851, vol. 132, No. 12.
Merrifield, "Solid Phase Peptide Synthesis. I. The Synthesis of a Tetrapeptide," J. Am. Chem. Soc. 1963, 85(14): 2149-2154.
Extended European Search Report for EP Application No. 18932859.4 dated Aug. 4, 2021 (7 pages).
Tanabe et al., "Crystal Structures of the Human Adiponectin Receptors," Nature, 2015, 312(520) (16 pages.).

* cited by examiner

*Primary Examiner* — Gina C Justice
(74) *Attorney, Agent, or Firm* — Merchant & Gould P.C.

(57) ABSTRACT

The present invention relates to a composition comprising adiponectin-derived peptide fragments and, more specifically, to a cosmetic composition and pharmaceutical composition for promoting hair growth comprising, as an active ingredient, one or more adiponectin-derived peptides selected from the group consisting of amino acid sequences of SEQ ID NOS: 1 to 21. The adiponectin-derived peptides activate the cell division of dermal papilla cells and outer root sheath cells of hair follicles, promote hair growth in the hair follicles, and also increase the expression of hair growth factors in the dermal papilla cells, and thus a composition of the present invention comprising the adiponectin-derived peptides can be effectively used to promote hair growth and inhibit hair loss.

3 Claims, 8 Drawing Sheets
Specification includes a Sequence Listing.

SEQUENCE LISTING

<160> NUMBER OF SEQ ID NOS: 23

<210> SEQ ID NO 1
<211> LENGTH: 4
<212> TYPE: PRT
<213> ORGANISM: Artificial Sequence
<220> FEATURE:
<223> OTHER INFORMATION: P4-1 peptide from adiponectin (IPGL)

<400> SEQUENCE: 1

Ile Pro Gly Leu
1

<210> SEQ ID NO 2
<211> LENGTH: 4
<212> TYPE: PRT
<213> ORGANISM: Artificial Sequence
<220> FEATURE:
<223> OTHER INFORMATION: P4-2 peptide from adiponectin (PGLY)

<400> SEQUENCE: 2

Pro Gly Leu Tyr
1

<210> SEQ ID NO 3
<211> LENGTH: 4
<212> TYPE: PRT
<213> ORGANISM: Artificial Sequence
<220> FEATURE:
<223> OTHER INFORMATION: P4-3 peptide from adiponectin (GLYY)

<400> SEQUENCE: 3

Gly Leu Tyr Tyr
1

<210> SEQ ID NO 4
<211> LENGTH: 4
<212> TYPE: PRT
<213> ORGANISM: Artificial Sequence
<220> FEATURE:
<223> OTHER INFORMATION: P4-4 peptide from adiponectin (LYYF)

<400> SEQUENCE: 4

Leu Tyr Tyr Phe
1

<210> SEQ ID NO 5
<211> LENGTH: 4
<212> TYPE: PRT
<213> ORGANISM: Artificial Sequence
<220> FEATURE:
<223> OTHER INFORMATION: P4-5 peptide from adiponectin (YYFA)

<400> SEQUENCE: 5

Tyr Tyr Phe Ala
1

<210> SEQ ID NO 6
<211> LENGTH: 4
<212> TYPE: PRT
<213> ORGANISM: Artificial Sequence
<220> FEATURE:
<223> OTHER INFORMATION: P4-6 peptide from adiponectin (YFAY)

<400> SEQUENCE: 6

Tyr Phe Ala Tyr
1

```
<210> SEQ ID NO 7
<211> LENGTH: 4
<212> TYPE: PRT
<213> ORGANISM: Artificial Sequence
<220> FEATURE:
<223> OTHER INFORMATION: P4-7 peptide from adiponectin (FAYH)

<400> SEQUENCE: 7

Phe Ala Tyr His
1

<210> SEQ ID NO 8
<211> LENGTH: 4
<212> TYPE: PRT
<213> ORGANISM: Artificial Sequence
<220> FEATURE:
<223> OTHER INFORMATION: P4-8 peptide from adiponectin (AYHI)

<400> SEQUENCE: 8

Ala Tyr His Ile
1

<210> SEQ ID NO 9
<211> LENGTH: 4
<212> TYPE: PRT
<213> ORGANISM: Artificial Sequence
<220> FEATURE:
<223> OTHER INFORMATION: P4-9 peptide from adiponectin (YHIT)

<400> SEQUENCE: 9

Tyr His Ile Thr
1

<210> SEQ ID NO 10
<211> LENGTH: 4
<212> TYPE: PRT
<213> ORGANISM: Artificial Sequence
<220> FEATURE:
<223> OTHER INFORMATION: P4-10 peptide from adiponectin (NIPG)

<400> SEQUENCE: 10

Asn Ile Pro Gly
1

<210> SEQ ID NO 11
<211> LENGTH: 4
<212> TYPE: PRT
<213> ORGANISM: Artificial Sequence
<220> FEATURE:
<223> OTHER INFORMATION: P4-11 peptide from adiponectin (CNIP)

<400> SEQUENCE: 11

Cys Asn Ile Pro
1

<210> SEQ ID NO 12
<211> LENGTH: 4
<212> TYPE: PRT
<213> ORGANISM: Artificial Sequence
<220> FEATURE:
<223> OTHER INFORMATION: P4-12 peptide from adiponectin (HCNI)

<400> SEQUENCE: 12

His Cys Asn Ile
1
```

<210> SEQ ID NO 13
<211> LENGTH: 4
<212> TYPE: PRT
<213> ORGANISM: Artificial Sequence
<220> FEATURE:
<223> OTHER INFORMATION: P4-13 peptide from adiponectin (palmitoyl-LYYF)

<400> SEQUENCE: 13

Leu Tyr Tyr Phe
1

<210> SEQ ID NO 14
<211> LENGTH: 5
<212> TYPE: PRT
<213> ORGANISM: Artificial Sequence
<220> FEATURE:
<223> OTHER INFORMATION: P3 peptide from adiponectin (IPGLY)

<400> SEQUENCE: 14

Ile Pro Gly Leu Tyr
1               5

<210> SEQ ID NO 15
<211> LENGTH: 5
<212> TYPE: PRT
<213> ORGANISM: Artificial Sequence
<220> FEATURE:
<223> OTHER INFORMATION: P4 peptide from adiponectin (PGLYY)

<400> SEQUENCE: 15

Pro Gly Leu Tyr Tyr
1               5

<210> SEQ ID NO 16
<211> LENGTH: 5
<212> TYPE: PRT
<213> ORGANISM: Artificial Sequence
<220> FEATURE:
<223> OTHER INFORMATION: P5 peptide from adiponectin (GLYYF)

<400> SEQUENCE: 16

Gly Leu Tyr Tyr Phe
1               5

<210> SEQ ID NO 17
<211> LENGTH: 5
<212> TYPE: PRT
<213> ORGANISM: Artificial Sequence
<220> FEATURE:
<223> OTHER INFORMATION: P6 peptide from adiponectin (LYYFA)

<400> SEQUENCE: 17

Leu Tyr Tyr Phe Ala
1               5

<210> SEQ ID NO 18
<211> LENGTH: 5
<212> TYPE: PRT
<213> ORGANISM: Artificial Sequence
<220> FEATURE:
<223> OTHER INFORMATION: P7 peptide from adiponectin (CNIPG)

<400> SEQUENCE: 18

Cys Asn Ile Pro Gly
1               5

```
<210> SEQ ID NO 19
<211> LENGTH: 5
<212> TYPE: PRT
<213> ORGANISM: Artificial Sequence
<220> FEATURE:
<223> OTHER INFORMATION: P8 peptide from adiponectin (KFHCN)

<400> SEQUENCE: 19

Lys Phe His Cys Asn
1               5

<210> SEQ ID NO 20
<211> LENGTH: 5
<212> TYPE: PRT
<213> ORGANISM: Artificial Sequence
<220> FEATURE:
<223> OTHER INFORMATION: P9 peptide from adiponectin (HCNIP)

<400> SEQUENCE: 20

His Cys Asn Ile Pro
1               5

<210> SEQ ID NO 21
<211> LENGTH: 5
<212> TYPE: PRT
<213> ORGANISM: Artificial Sequence
<220> FEATURE:
<223> OTHER INFORMATION: P10 peptide from adiponectin (NIPGL)

<400> SEQUENCE: 21

Asn Ile Pro Gly Leu
1               5

<210> SEQ ID NO 22
<211> LENGTH: 18
<212> TYPE: PRT
<213> ORGANISM: Artificial Sequence
<220> FEATURE:
<223> OTHER INFORMATION: P1 peptide from adiponectin
      (KFHCNIPGLYYFAYHITV)

<400> SEQUENCE: 22

Lys Phe His Cys Asn Ile Pro Gly Leu Tyr Tyr Phe Ala Tyr His Ile
1               5                   10                  15

Thr Val

<210> SEQ ID NO 23
<211> LENGTH: 8
<212> TYPE: PRT
<213> ORGANISM: Artificial Sequence
<220> FEATURE:
<223> OTHER INFORMATION: P2 peptide from adiponectin (IPGLYYFA)

<400> SEQUENCE: 23

Ile Pro Gly Leu Tyr Tyr Phe Ala
1               5
```

COMPOSITION FOR PROMOTING HAIR GROWTH COMPRISING ADIPONECTIN-DERIVED PEPTIDE

This application is a National Stage Application of PCT/KR2018/010236, filed 3 Sep. 2018, which application is incorporated herein by reference. To the extent appropriate, a claim of priority is made to the above disclosed application.

TECHNICAL FIELD

The present invention relates to a composition for promoting hair growth comprising peptide fragments (or small peptides) derived from adiponectin.

BACKGROUND ART

Human hairs are about 1.3 million or more, and scalp hairs are 100,000 to 150,000, and each hair has different cycles, and grows, is kept, and removed through three stages of the anagen (the active growth phase), the catagen (the apoptotic regression phase), and the telogen (the resting phase). These cycles are repeated over 3 to 6 years, and as a result, an average of 50 to 100 hairs per day is normally removed. In general, the term 'hair loss' means a condition with less or no hairs than normal due to some reasons.

Today, the causes of hair loss include internal factors such as the action of male hormones, and external factors such as mental stress in daily life and accumulation of lipid peroxidation in the scalp, and these factors are known to be involved in a complex manner to indicate hair loss symptoms. In recent years, not only male-pattern hair loss, but also female hair loss population are increasing due to an increase in stress caused by changes in dietary life and social environment, and the population suffering from such abnormal symptoms of scalp and hair is gradually increasing, and the age is also getting lower.

When describing the effects of male hormones on hair loss, among the factors, testosterone binds to a 5α-reductase enzyme in the body to produce dihydroxytestosterone (hereinafter referred to as 'DHT'), and this DHT binds to an androgen receptor in the hair root to have a dominant effect in inhibiting the production of hair follicles of the hair root. Therefore, studies to develop a substance for preventing hair loss using an inhibitor of the 5α-reductase enzyme are currently being actively conducted. In addition to the enzyme action, the hair loss may also occur due to lack of nutrition, scalp dryness, stress, etc. In the case of the hair loss caused by these causes, sufficient nutrition, scalp management, and intake or administration of antioxidants may prevent hair loss and promote hair growth (Korea Patent Publication No. 10-2016-0070508).

As a hair growth agent currently on the market, a preparation containing main ingredients such as minoxidil from Upzone of the United States and trichosaccharide from Crinos, Co. of Italy has been used, but the absence of distinct effects and side effects problems are emerging. In addition, Propecia (ingredient name: finasteride), which was developed by Merck as a therapeutic agent for prostatic hyperplasia and then introduced to the treatment of hair loss, is known as a substance for inhibiting the activity of 5α-reductase, an enzyme that acts on the metabolism of the male hormone testosterone in hair follicles, but needs to be administered continuously, and has a problem that cause side effects such as decreased sexual function, allergies, and depression.

In addition, since female hair loss is known to occur due to multiple causes, known as one of the causes, such as blood disorders in the scalp occurring as aging progresses because the developing of the scalp stops faster than that of the skull, there was a problem that narrow treatment such as hormone suppression as described above was only a short-sighted prescription.

In consideration of these problems, research has been conducted on a composition for preventing hair loss or promoting hair growth that does not cause side effects even when used for a long time without toxicity by containing an extract derived from a natural substance as an active ingredient. However, in the case of related products containing the extract derived from the natural substance, there were many cases that were insufficient to exhibit an effect for preventing hair loss, promoting hair growth, and improving hairs at an expected level (Korean Patent Publication No. 10-2016-0021086).

On the other hand, adiponectin is a type of adipocaine, a protein hormone specifically secreted by adipocytes, and plays an important role to adjust ardiovascular diseases such as hyperglycemia, hyperinsulinism, obesity, and arteriosclerosis by enhancing the function of insulin and inducing insulin resistance. In addition, the adiponectin has a function of inhibiting metastasis and inflammatory response of cancer cells. The adiponectin not only proliferates keratinocytes, but also promotes the expression of filaggrin, hyaluronic acid and the extracellular matrix in the skin, thereby performing functions such as wound healing, fibrosis inhibition, skin wrinkle improvement, and moisturizing (Korean Patent Publication No. 10-2015-0032401). In addition, it is disclosed that the adiponectin has an effect of promoting hair growth in vitro.

The adiponectin consists of 244 amino acids and consists of a signal sequence, a collagen-like domain located at an N-terminus and a C1q-like globular domain located at a C-terminus. A hexamer and a high molecular complex (HMW complex) of 400 kDa are known to be main oligomers, and the HMW complex is known to be more active than a low molecular complex (LMW complex).

The development of adiponectin-derived peptides, which are known to have various physiological activities in the related art, has been targeted by many domestic and foreign researchers and pharmaceutical companies, but the possibility of final success was relatively low due to difficulties in forming polymers in the body. Therefore, there is a need to develop short adiponectin-derived peptides that can be applied to the skin and have excellent physiological activity.

DISCLOSURE

Technical Problem

An object of the present invention is to provide a composition for promoting hair growth comprising adiponectin-derived peptides.

Technical Solution

In order to solve the above problems, the present invention provides a cosmetic composition or pharmaceutical composition for promoting hair growth including, as an active ingredient, one or more adiponectin-derived peptides selected from the group consisting of amino acid sequences of SEQ ID NOS: 1 to 21.

According to one embodiment of the present invention, the composition of the present invention preferably includes, as an active ingredient, one or more adiponectin-derived peptides selected from the group consisting of SEQ ID NOS: 16 and 21, but is not limited thereto.

According to one embodiment of the present invention, the adiponectin-derived peptides may be included in the cosmetic composition or pharmaceutical composition at a concentration of 0.001 mM to 20 mM, but is not limited thereto.

According to another embodiment of the present invention, the cosmetic composition may be selected from formulations, such as a scalp treatment agent, a soap, a hair tonic, a shampoo, a rinse, a hair pack, a hair gel, a lotion, a conditioner, hair oil, mousse, cream, a solid agent, a solution, an emulsion, a dispersant, a micelle, liposome, an ointment, a toner, an essence, a patch, or a spray, but is not limited thereto.

Further, the present invention provides a method for promoting hair growth including treating or administering, to a subject, one or more of adiponectin-derived peptides selected from the group consisting of amino acid sequences of SEQ ID NOS: 1 to 21 in a pharmaceutically or cosmetically effective dose.

According to one embodiment of the present invention, the subject may be a human, but is not limited thereto.

Advantageous Effects

The present invention relates to a composition comprising adiponectin-derived peptides having an effect of promoting hair growth. The adiponectin-derived peptides activate the cell division of dermal papilla cells and outer root sheath cells of hair follicles, promote hair growth in the hair follicles, and also increase the expression of hair growth factors in the dermal papilla cells, and thus, the composition of the present invention comprising the adiponectin-derived peptides can be effectively used to promote hair growth and inhibit hair loss.

BEST MODE

Figure 1:
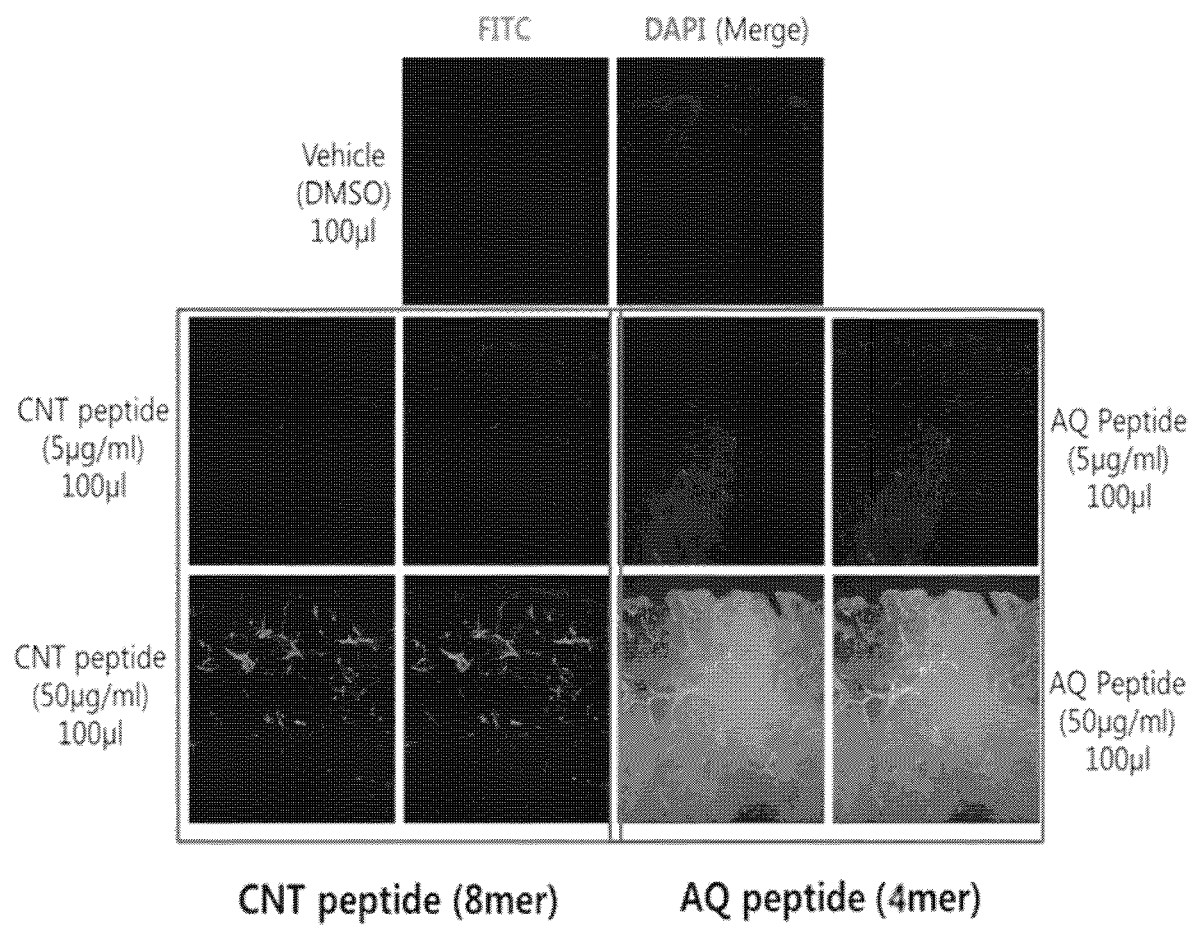
FIG. 1 is a photograph showing a result of a skin permeability test for adiponectin-derived peptides of the present invention.

In order to solve the object, the present invention provides a cosmetic composition or pharmaceutical composition for promoting hair growth including, as an active ingredient, one or more adiponectin-derived peptides selected from the group consisting of amino acid sequences of SEQ ID NOS: 1 to 21.

The adiponectin-derived peptides of the present invention are peptide fragments having lengths of 4 amino acids (4-mer) or amino acids (5-mer) derived from adiponectin, and have amino acid sequences shown in Table 1 below.

TABLE 1

| Adiponectin peptide | Amino acid sequence (molecular weight) | SEQ ID NO: | Adiponectin peptide | Amino acid sequence (molecular weight) | SEQ ID NO: |
|---|---|---|---|---|---|
| P4-1 | IPGL (398.5) | 1 | P1 | KFHCNIPGLYYF AYHITV (2186.6) | 22 |
| P4-2 | PGLY (448.52) | 2 | P2 | IPGLYYFA (943) | 23 |
| P4-3 | GLYY (514.58) | 3 | P3 | IPGLY (561) | 14 |
| P4-4 | LYYF (604.71) | 4 | P4 | PGLYY (611) | 15 |
| P4-5 | YYFA (562.63) | 5 | P5 | GLYYF (662) | 16 |
| P4-6 | YFAY (562.63) | 6 | P6 | LYYFA (676) | 17 |
| P4-7 | FAYH (536.59) | 7 | P7 | CNIPG (503) | 18 |
| P4-8 | AYHI (502.57) | 8 | P8 | KFHCN (647) | 19 |
| P4-9 | YHIT (532.6) | 9 | P9 | HCNIP (582) | 20 |
| P4-10 | NIPG (399.44) | 10 | P10 | NIPGL (512) | 21 |
| P4-11 | CNIP (445.54) | 11 | | | |
| P4-12 | HCNI (485.56) | 12 | | | |
| P4-13 | Palmitoyl-LYYE | 13 | | | |

According to one embodiment of the present invention, the adiponectin-derived peptides are preferably contained at a concentration of 0.001 mM to 20 mM in the cosmetic composition, and more preferably contained at a concentration of 0.01 mM to 10 mM, but are not limited thereto. When the concentration of the peptides is less than 0.001 mM, it is difficult to obtain an effect of promoting hair growth or inhibiting hair loss, and when the concentration thereof exceeds 20 mM, there is a problem in that the production economy is deteriorated because no apparent increase in the effect due to the increase in content is shown.

The peptides of the present invention may be prepared by general chemical synthesis, for example, solid-phase peptide synthesis, and may also be prepared by culturing a microorganism transformed with a recombinant vector containing nucleic acids encoding the peptides, expressing the peptides, and then purifying the peptides by a conventional method, but the method is not limited thereto.

In addition to the peptides, the cosmetic composition according to the present invention may additionally contain other ingredients that may give a synergistic effect to the effect of the peptides within a range that does not impair a desired effect of the present invention. For example, the cosmetic composition of the present invention may include not only any other substances known to promote hair growth, but also general auxiliary agents such as antioxidants, stabilizers, solubilizers, vitamins, pigments and fragrances, or carriers.

The cosmetic composition of the present invention is not particularly limited in its formulation, and may be prepared in any formulation commonly prepared in the art, for example, may be formulated by a solution, a suspension, an emulsion, a paste, a gel, a cream, a lotion, a powder, a soap, a surfactant-containing cleansing, oil, a powder foundation, an emulsion foundation, a wax foundation, a spray, and the like. Meanwhile, the cosmetic composition may also be prepared by formulations, such as a scalp treatment agent, a soap, a hair tonic, a shampoo, a rinse, a hair pack, a hair gel, a lotion, a conditioner, hair oil, mousse, a cream, a solid agent, a solution, an emulsion, a dispersant, a micelle, liposome, an ointment, a toner, an essence, a patch, or a spray.

When the formulation of the cosmetic composition is the paste, cream, or gel, animal oil, as a carrier ingredient, vegetable oil, wax, paraffin, starch, tragacanth, cellulose derivatives, polyethylene glycol, silicone, bentonite, silica, talc, or zinc oxide is used. In the case of the powder or spray, lactose, talc, silica, aluminum hydroxide, calcium silicate or polyamide powder may be used as the carrier ingredient. Particularly, in the case of the spray, a propellant such as chlorofluorohydrocarbon, propane/butane or dimethyl ether may additionally be included.

When the formulation of the present invention is the solution or emulsion, as the carrier ingredient, a solvent, a solubilizing agent or an emulsifying agent may be used. For example, the carrier ingredient includes water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or fatty acid ester of sorbitan.

When the formulation of the present invention is the suspension, as the carrier ingredient, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, or the like may be used. In the case of the surfactant-containing cleansing, as the carrier ingredient, aliphatic alcohol sulfate, aliphatic alcohol ether sulfate, sulfosuccinic acid monoester, isethionate, imidazolinium derivatives, methyltaurate, sarcosinate, fatty acid amide ether sulfate, alkylamido betaine, aliphatic alcohol, fatty acid glyceride, fatty acid diethanolamide, vegetable oil, lanolin derivatives, ethoxylated glycerol fatty acid ester, or the like may be used.

Figure 2:
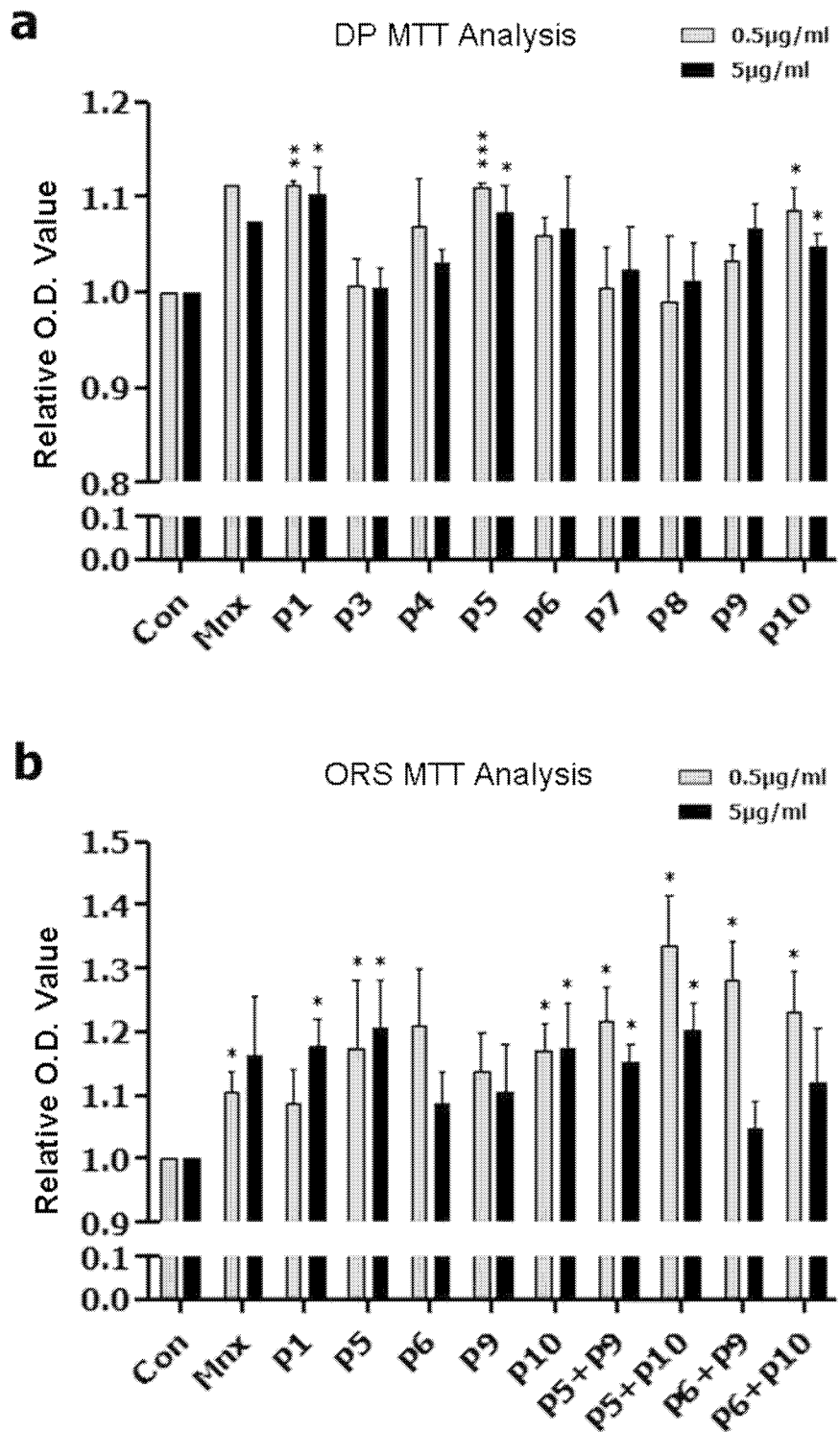
FIG. 2 is a graph showing an effect of the adiponectin-derived peptides of the present invention on the cell division and activation in human hair follicles-derived dermal papilla cells and outer root sheath cells, wherein Con represents a negative control, Mnx represents minoxidil used as a positive control, P1 and P2 represent adiponectin peptide positive controls, and P3 to P10 represent adiponectin-derived peptides prepared in the present invention.
Figure 3:
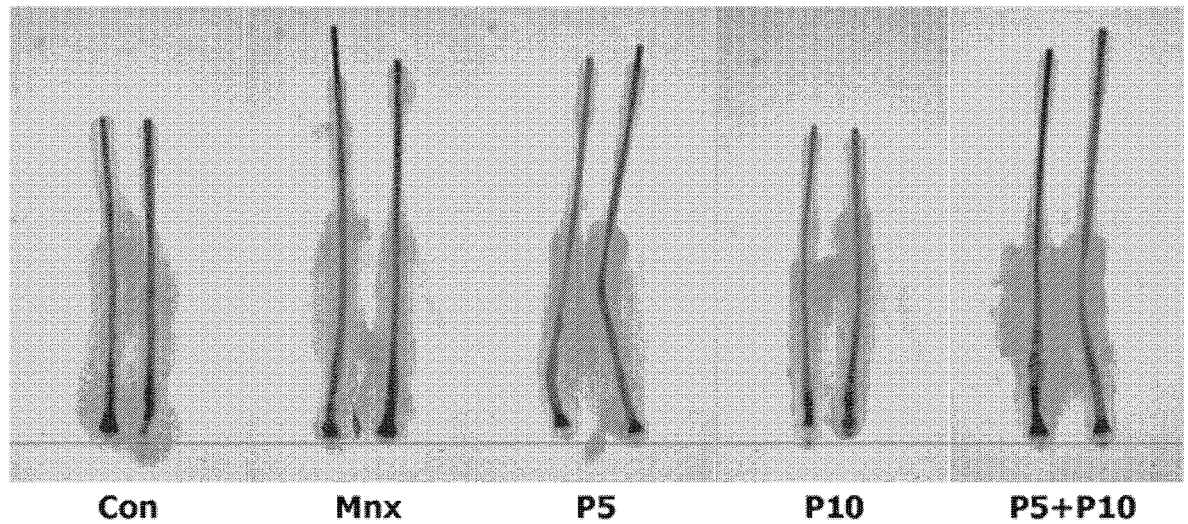
FIG. 3 is a graph and a photograph showing an effect of the adiponectin-derived peptides of the present invention on the growth of human hair follicles.
Figure 3:
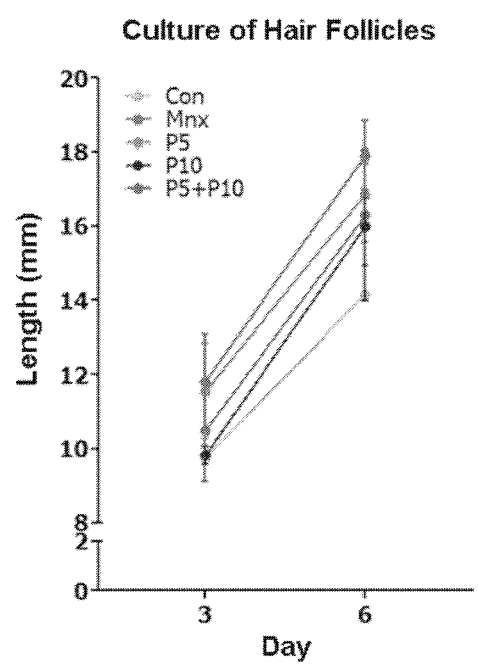

According to a specific embodiment of the present invention, the adiponectin-derived peptides of the present invention have remarkably excellent permeability to the skin (see FIG. 1), promote the cell division of dermal papilla cells and outer root sheath cells (see FIG. 2), and promote the growth of hair follicles (see FIG. 3).

Figure 5:
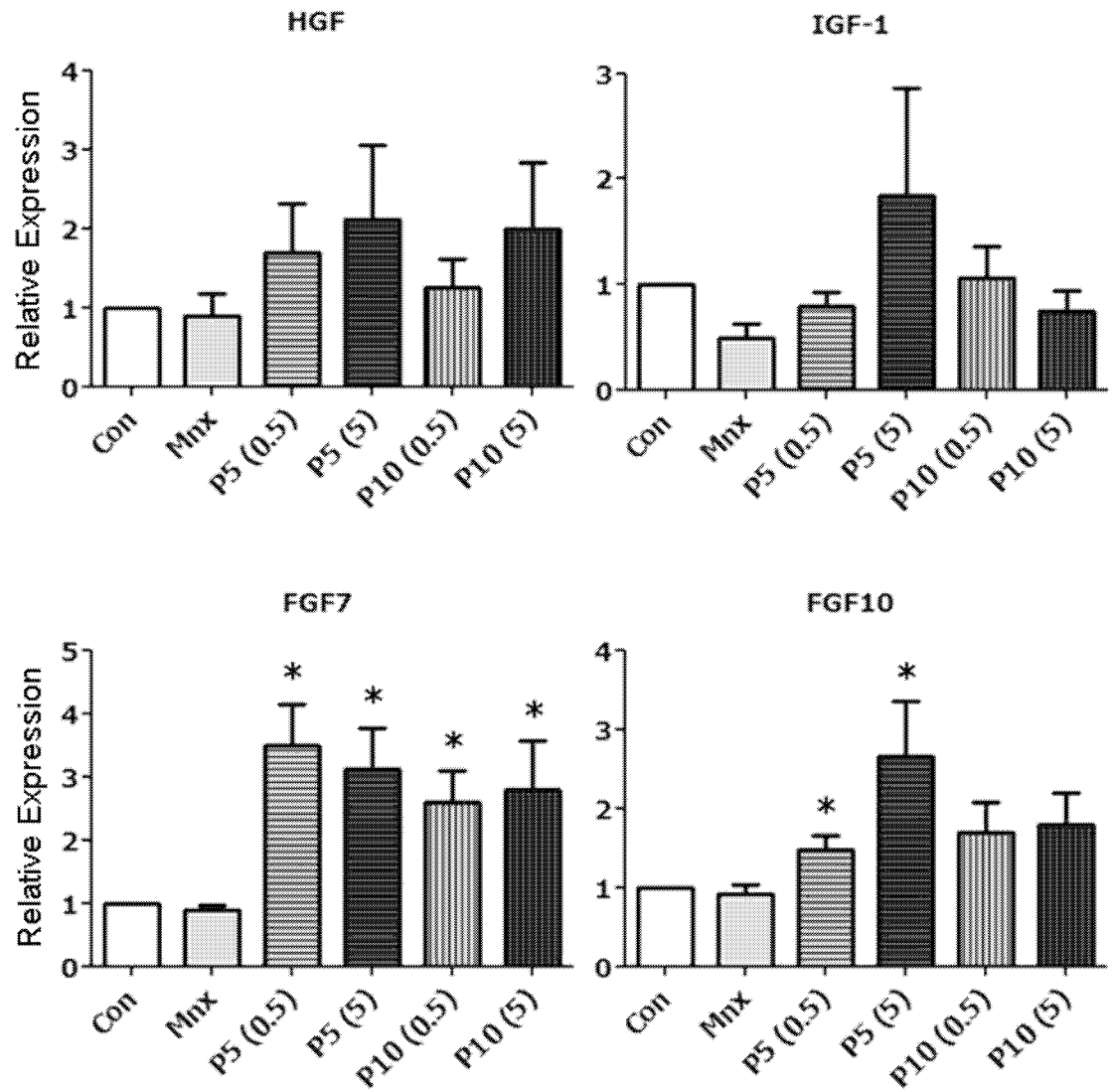
FIG. 5 is a graph showing an effect of the adiponectin-derived peptides of the present invention on the expression of hair growth factors in dermal papilla cells of human hair follicles.
Figure 6:
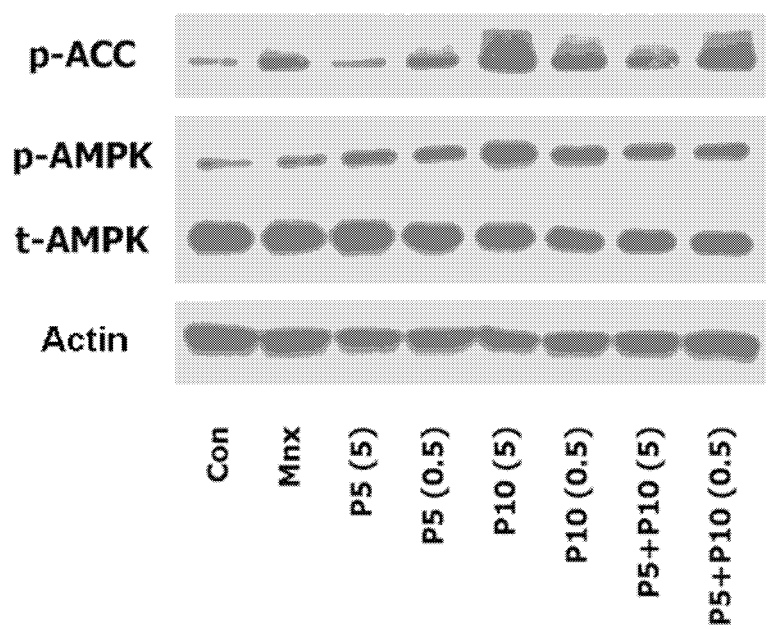
FIG. 6 is an electrophoretic photograph showing an effect of the adiponectin-derived peptides of the present invention on the phosphorylation of sub-signaling proteins of adiponectin receptors in human outer root sheath cells.

In addition, according to another specific embodiment of the present invention, the adiponectin-derived peptides of the present invention increase the expression of hair growth factors such as FGF7, FGF10, HGF, IGF, etc. in dermal papilla cells of human hair follicles (see FIG. 4), increase the phosphorylation of sub-signaling proteins of adiponectin receptors in human outer root sheath cells (see FIG. 5), and may significantly induce the hair growth phase (see FIG. 6).

Accordingly, the adiponectin-derived peptides of the present invention activate the cell division of dermal papilla cells and outer root sheath cells of hair follicles, promote hair growth in the hair follicles, and also increase the expression of hair growth factors in the dermal papilla cells, and thus, the composition of the present invention comprising the adiponectin-derived peptides can be effectively used as an active ingredient of the cosmetic composition to promote hair growth and inhibit hair loss.

On the other hand, the route of administration of the pharmaceutical composition for promoting hair growth according to the present invention includes skin, oral, intravenous, intramuscular, intraarterial, transdermal, subcutaneous, intraperitoneal, intranasal, intestinal, topical, sublingual or rectal route, preferably oral or parenteral administration, but is not limited thereto. The "parenteral" includes subcutaneous, intradermal, intravenous, intramuscular, intralesional injection or infusion techniques.

The pharmaceutical composition of the present invention may contain one or more active ingredients exhibiting the same or similar function in addition to the adiponectin-derived peptides according to the present invention. The composition may be formulated and used in the form of oral formulations such as powders, granules, tablets, capsules, suspensions, emulsions, syrups, etc., external preparations, suppositories, and sterile injectable solutions according to a general method, respectively.

Solid preparations for oral administration include powders, granules, tablets, capsules, soft capsules, pills, and the like. Liquid preparations for oral administration may correspond to suspensions, oral liquids, emulsions, syrups, and the like, and may include various excipients, for example, a wetting agent, a sweetener, an aromatic agent, a preservative, and the like, in addition to water and liquid paraffin which are commonly used as simple diluents. Preparations for parenteral administration may be formulated and used in the forms of external preparations such as powders, granules, tablets, capsules, sterilized aqueous solutions, solutions, non-aqueous solutions, suspensions, emulsions, syrups, suppositories, aerosols, etc., and sterile injectable preparations according to a general method, respectively. Preferably, a pharmaceutical composition for skin external use such as cream, gel, patch, spray, ointment, emplastrum, lotion, liniment, pasta, or cataplasma may be prepared and used, but is not limited thereto. As the non-aqueous solution and the suspension, propylene glycol, polyethylene glycol, vegetable oil such as olive oil, injectable ester such as ethyl oleate, and the like may be used. As a base of the suppository, witepsol, macrogol, tween 61, cacao butter, laurinum, glycerogelatin, and the like may be used.

The composition may additionally contain an adjuvant such as a preservative, a stabilizer, a hydrating agent or an emulsification accelerator, a salt and/or a buffer for controlling the osmotic pressure, and other therapeutically useful substances, and may be formulated according to a general method, such as mixing, granulating or coating.

The pharmaceutical composition of the present invention may vary according to various factors including the age, weight, general health, and sex of a subject, an administration time, a route of administration, an excretion rate, a drug combination, and the severity of a specific disease.

In the case of formulating the pharmaceutical composition containing the adiponectin-derived peptides of the present invention as an active ingredient in a unit dosage form, the adiponectin-derived peptides as the active ingredient are preferably contained in a unit dose of about 0.01 mg to 1,500 mg, and the dosage required for adult treatment is usually in the range of about 1 mg to 500 mg per day depending on the frequency and intensity of administration, but it is not limited thereto. When administered intramuscularly or intravenously to adults, a total dose of about 5 mg to 300 mg per day is usually sufficient as a single dose, but a higher daily dose may be preferable for some patients. The composition of the present invention may be used alone or in combination with surgery, radiation therapy, hormone therapy, chemotherapy, and methods of using biological response modifiers.

Further, the present invention provides a method for promoting hair growth including treating or administering, to a subject, one or more adiponectin-derived peptides selected from the group consisting of amino acid sequences of SEQ ID NOS: 1 to 21 in a pharmaceutically or cosmetically effective dose.

The pharmaceutically or cosmetically effective dose is 0.0001 mg/kg to 100 mg/kg, preferably 0.001 mg/kg to 10 mg/kg, but is not limited thereto. The treatment or administration amount may be adjusted according to the weight, age, sex, and health condition of a specific patient, diet, an administration period, an administration method, an elimination rate, the severity of disease, etc. The treatment or administration may be performed once a day or several times a day.

The subject is vertebrate animals, preferably mammals, more preferably human or experimental animals such as mouse, rabbit, guinea pig, hamster, dog, and cat, and most preferably the human, but is not limited thereto.

In the treatment or administration method, the composition may be applied, or orally or parenterally administered, and in the parenteral administration, the composition may be administered by intraperitoneal injection, rectal injection, subcutaneous injection, intravenous injection, intramuscular injection, intrauterine dural injection, cerebrovascular injection or intrathoracic injection.

Hereinafter, the present invention will be described in more detail through Examples.

However, the following Examples are just illustrative of the present invention, and the contents of the present invention are not limited to the following Examples.

Example 1. Preparation of Adiponectin-Derived Peptides

In order to synthesize peptides of the present invention, Merrifield's solid phase peptide synthesis (SPPS) method (J. Am. Chem. Soc., 85(14), 2149-2154) was used. First, for the synthesis of the peptides of the present invention, the synthesis was started using a 2-chlorotrityl chloride (CTC) resin, and 9-fluorenylmethoxy carbonyl (Fmoc) amino acid in a first step was coupled using N,N-diisopropylethylamine (DIEA) under a dichloromethane (DCM) solvent. Fmoc amino acids in the next step were coupled using N,N-diisopropylethylamine (DIEA) together with N-[(dimethylamino-)-1H-1,2,3-triazolo[4,5-b]pyridin-1-yl-methylene]-N-methylmethanaminium hexafluorophosphate N-oxide (HATU) and 1-hydroxy-7-azabenzotriazole (HOAt) or N-[(1H-benzotriazol-1-yl) (dimethylamino)methylene]-N-methylmethanamiminium hexafluorophosphate N-oxide (HBTU) and hydroxybenzotriazole (HOBt) to extend chains of the peptides. At this time, the synthesis was performed from a C-terminus to an N-terminus, and after the Fmoc-amino acid was coupled to the amino terminus, and then the Fmoc group was removed with a 20% piperidine solution (Solid-Phase Synthesis: A Practical Guide (1 ed.). CRC Press.848), and washed several times with dimethylformamide (DMF), and then the coupling was performed. Finally, after coupling the Fmoc-amino acid, the Fmoc group was removed with a 20% piperidine solution, and an acyl group was coupled by using carboxylic acid and N,N'-diisopropyl carbodiimide (DIC), 1-hydroxy-7-azabenzo Triazole (HOAt) together, and then washed several times with DMF and dried. Here, a trifluoroacetic acid (TFA)-$H_2O$-triisopropylsilane (95:2.5:2.5, vol./vol.) solution was added and reacted for 2 to 3 hours to remove a protecting group and to separate the peptides from the resin, and then the peptides were immersed in diethylether to synthesize the peptides having amino acid sequences shown in Table 1 above, respectively.

The crude peptides obtained by the above method were confirmed for purity using RP-HPLC (2996 Detector, 515 Pump, Waters) with a gradient solvent composition of 0.1% TFA-containing acetonitrile and water. As a result, the peptides having purity of 95% or less were separated and purified by Prep-LC to obtain the peptides having purity of 97% or more. As a result of elemental analysis with an elemental analyzer (EA1112, CE Instrument, Italy) to confirm exact ingredients of the peptides, it was confirmed that the elemental content of the peptide coincided with the elemental content calculated from the amino acid sequence to have the correct amino acid sequence.

Example 2. Measurement of Skin Permeability of Adiponectin-Derived Peptides

Adiponectin was decomposed into smaller units including globular domains, and subunits having globular domains were more active than adiponectin having a full length, and these receptors for adiponectin were known as adiponectin receptor 1 (AdipoR1) and adiponectin receptor 2 (AdipoR2) (Crystal structures of the human adiponectin receptors. Nature. 2015 Apr. 16; 520(7547):312-6.doi:10.1038/nature14301). Accordingly, the skin permeability of the adiponectin-derived peptide of the present invention prepared in Example 1 was most similar to that of the human skin, and was verified using pig skin, which was generally used in a permeability test. After cutting the pig skin into sizes having a width and a height of 2 cm, the corresponding peptide stock with FITC fluorescence (positive controls of 8-mer-long peptide 2, 4-mer peptide 4) and DMSO were prepared by concentration, and the sufficient amount was applied on the pig skin. The light was blocked and the pig skin was placed in an incubator at 37° C. for 2 hours. After rapid freezing with LN2, cryosection was performed. DAPI (nuclear staining) was treated for 5 minutes and then washed, and observed with a confocal microscope.

As a result, it was confirmed that the adiponectin-derived peptides of the present invention had remarkably excellent permeability to the skin compared to an 8 amino acids-long peptide used as a control (FIG. 1).

Example 3. Effect of Adiponectin-Derived Peptides on Cell Division and Activation in Human Hair Follicles-Derived Dermal Papilla Cells and Outer Root Sheath Cells Primary cultured human hair follicles-derived dermal papilla cells and outer root sheath cells were subcultured to passages 2 to 3, and then treated with minoxidil, which has been conventionally used as an agent for preventing hair loss and treating hair growth as a positive control at a concentration of 1 mM, and separately treated with the adiponectin-derived peptide of the present invention prepared in Example 1 at concentrations of 0.5 µg/ml and 5 µg/ml. After 48 hours, the activated living cells were stained with an MTT solution and compared with a negative control group, and the degree of division and activation of the cells was confirmed.

As a result, it was confirmed that the adiponectin-derived peptides of the present invention promoted the cell division of dermal papilla cells and outer root sheath cells, and particularly, among the adiponectin-derived peptides, peptides P5 and P10 and a combination of the two peptides had a more excellent effect than minoxidil used as a positive control (FIG. 2).

Example 4. Effect of Adiponectin-Derived Peptides on Growth of Human Hair Follicles Human hair follicles obtained from volunteers were used to perform an organ culture test of hair follicles in vitro. Minoxidil, which has been conventionally used as an agent for preventing hair loss and treating hair growth was treated as a positive control at a concentration of 1 mM, the adiponectin-derived peptide of the present invention prepared in Example 1 was separately treated at a concentration of 5 µg/ml, and an effect on the growth of human hair follicles was confirmed. After the human hair follicles culture experiment, the lengths of hairs grown on day 3 and day 6 were measured and compared with the negative control group, and then the effect of promoting the hair growth of the human hair follicles was conformed.

Figure 4:
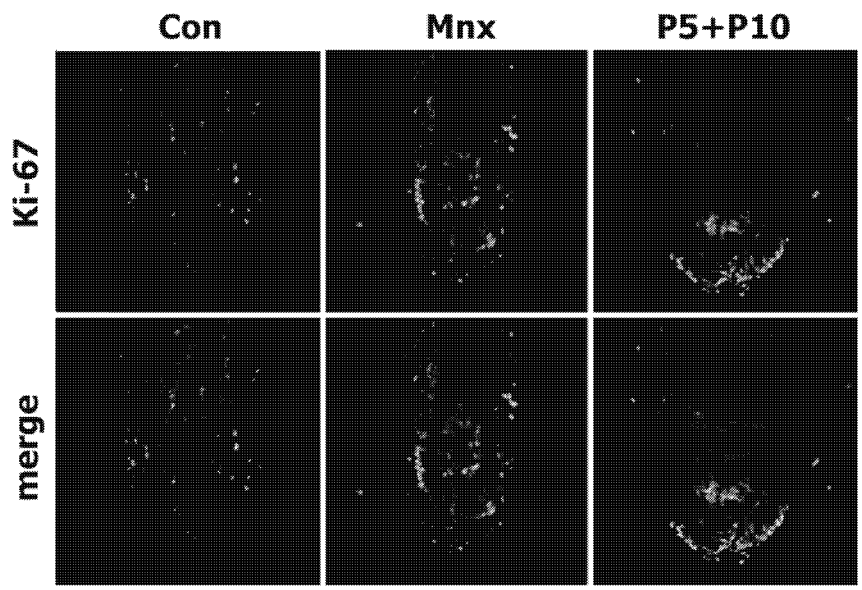
FIG. 4 is a fluorescence staining photograph of Ki-67 positive cells expressed around hair follicles treated with the adiponectin-derived peptides of the present invention.

As a result, the adiponectin-derived peptides of the present invention promoted the growth of hair follicles, and particularly, among the adiponectin-derived peptides, an adiponectin peptide combined with peptides P5 and P10 more significantly promoted the hair growth than minoxidil used as a positive control (FIG. 3). In addition, the hair follicles were rapidly frozen and then sectioned into tissue sections, cells in tissues were labeled using a Ki-67 antibody, which was a marker of cell division and activation and labeled with fluorescence using a fluorescent secondary antibody capable of detecting the Ki-67 antibody, and then the number of Ki-67-positive cells expressed around hair follicles was checked using a fluorescence microscope in a dark room. As a result, it was confirmed that in the adiponectin peptide group combined with P5 and P10, the number of Ki-67-positive cells significantly increased compared to a negative control group (FIG. 4).

Example 5. Effect of Adiponectin-Derived Peptides on Expression of Hair Growth Factors in Dermal Papilla Cells of Human Hair Follicles Primary cultured human hair follicles-derived dermal papilla cells were subcultured to passages 2 to 3, and then treated with minoxidil, which has been conventionally used as an agent for preventing hair loss and treating hair growth as a positive control at a concentration of 1 mM, and separately treated with the adiponectin-derived peptide of the present invention prepared in Example 1 at concentrations of 0.5 µg/ml and 5 µg/ml. After 3 hours, mRNA was extracted from dermal papilla cells, synthesized again to cDNA, and as compared with a negative control group, an effect on the expression of FGF7, FGF10, HGF and IGF known as hair growth factors was conformed using a real-time quantitative PCR method.

As a result, the adiponectin-derived peptides of the present invention increased the expression of FGF7, FGF10, HGF and IGF, and in particular, the expression of FGF7 and FGF10, which were known as the most important hair growth factors, was significantly more increased than minoxidil used as a positive control (FIG. 5).

Example 6. Effect of Adiponectin-Derived Peptides on Phosphorylation of Sub-Signaling Proteins of Adiponectin Receptors in Human Outer Root Sheath Cells In order to confirm whether the adiponectin peptide actually acted through the adiponectin receptor, primary cultured human hair follicles-derived outer root sheath cells were divided into a group treated with an adiponectin receptor inhibitor and a non-treated group, and the groups were treated with the adiponectin-derived peptide prepared in Example 1 as a combination of P5 and P10 at concentrations of 0, 0.05, 0.1, 0.5, 1, 5, and 10 µg/ml, respectively. As a positive control, adiporon (AdipoR agonis), a selective agonist of adiponectin receptors such as AdipoR1 and AdipoR2, was treated. After 10 minutes, only the proteins were extracted from the cells, purified, and then the amounts of proteins were uniformly quantified. Thereafter, each protein was separated by size using a Western blot method, and detected using an antibody specific for a target protein, and then colored using a peroxidase method. Through this, the effect on the phosphorylation of acetyl-CoA carboxylase (ACC) and AMP-activated protein kinase (AMPK), which were sub-signaling proteins of adiponectin receptors such as AdipoR1 and AdipoR2, was confirmed.

As a result, it was confirmed that the adiponectin-derived peptides of the present invention remarkably increased the phosphorylation of ACC and AMPK, the sub-signaling proteins of the adiponectin receptors, at the same level as the adiporon used as a positive control (FIG. 6).

Example 7. Effect of Adiponectin-Derived Peptides on Induction of Hair Growth Phase It was known that in a mouse of 7 to 8 weeks of age, all hairs entered the resting phase and then the hairs were converted to the hair growth phase. Then, the effect of the adiponectin-derived peptides of the present invention on the growth phase inducing process was confirmed using C57BL/6 mice. 3% minoxidil, which has been conventionally used as an agent for preventing hair loss and treating hair growth, and a combination of the adiponectin-derived peptides P5 and P10 prepared in Example 1 were applied to the lower back skin of the mouse at a concentration of 0.1 mM once a day and then the hair growth was confirmed.

Figure 7:
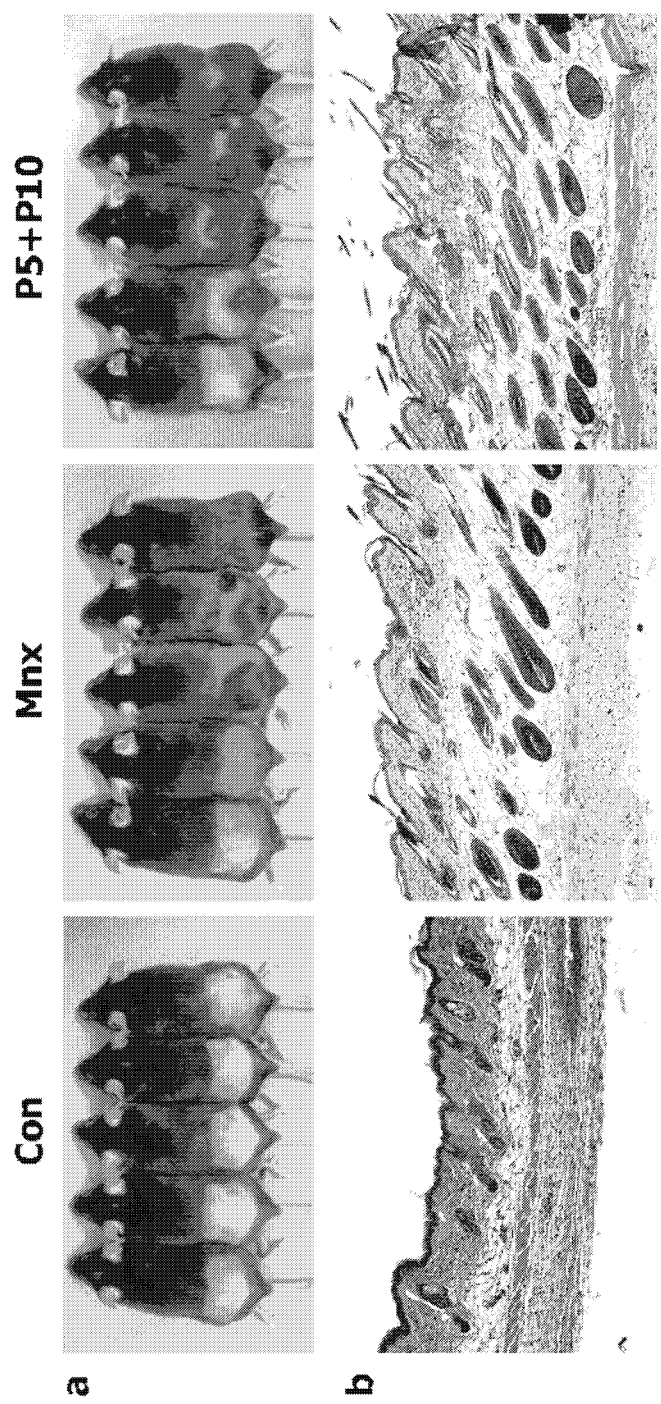
FIG. 7 is a photograph showing an effect of the adiponectin-derived peptides of the present invention on the induction of a hair growth phase.

As a result, after about 3 weeks, a ratio of an area where the hairs in the growth phase were grown among areas where the hairs were first removed was significantly increased in a group treated with the adiponectin-derived peptide of the present invention. Thereafter, when a biopsy of the corresponding area was performed to evaluate the formation of hair follicles in the growth phase, it was confirmed that even in a group to which the adiponectin-derived peptide was applied, the formation of hair follicles was promoted similarly to a group treated with minoxidil, which was used as a positive control (FIG. 7).

Example 8. Confirmation of Structure of Adiponectin Peptide in Adiponectin Protein and Action Possibility Through Polymer Formation In Vivo By analyzing a three-dimensional structure of an adiponectin protein present in the human, a structural position of the adiponectin peptide prepared in the present invention and the action possibility of an adiponectin receptor in vivo were analyzed.

Figure 8:
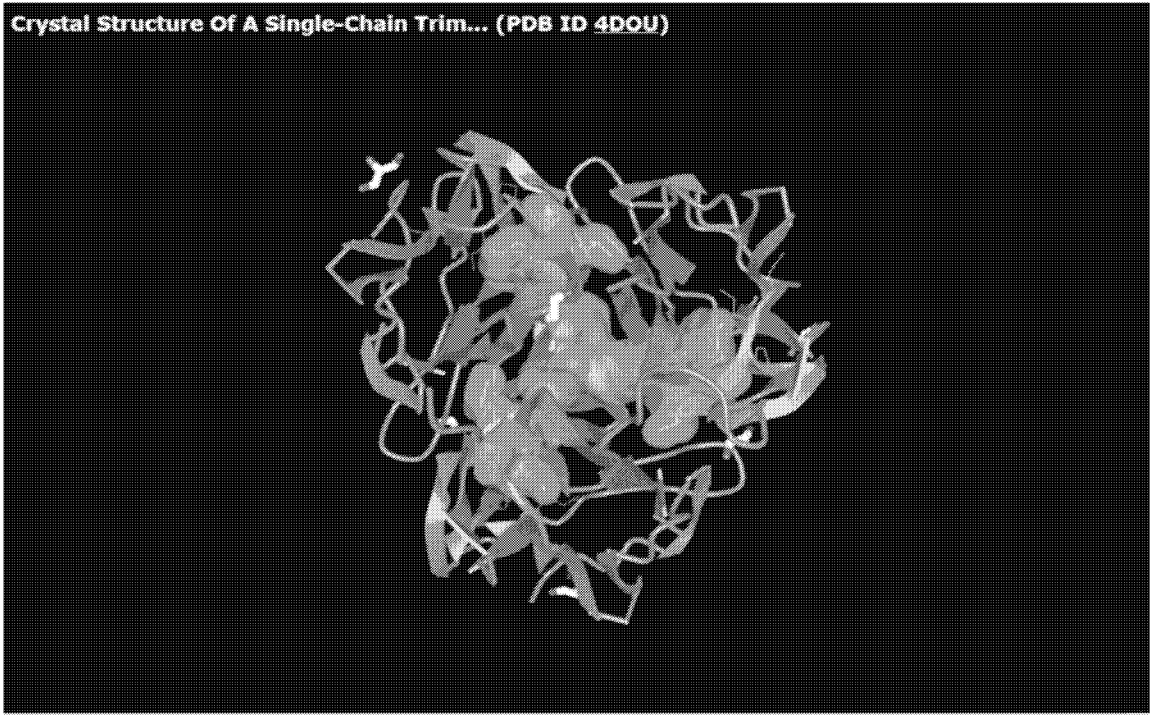
FIG. 8 shows a crystal structure of a structural position in which the adiponectin peptides of the present invention exist in the adiponectin protein.

As a result, in the case of the adiponectin peptide, it was found that the adiponectin peptide was present in the form of a trimer by repeating a total of 3 times in a globular domain known as an action site of the adiponectin protein. Particularly, since the action site was distributed on the outermost side of the globular structure of the globular domain, the possibility of actually acting on the adiponectin receptor was high. In particular, in the case of the P5 peptide, it was confirmed that a peptide sequence repeated three times in the adiponectin protein formed a polymer when describing the three-dimensional protein structure. When the polymer consisted of lipophilic amino acids inside the polymer and hydrophilic amino acids outside the polymer and a lot of hydrophilic substances were actually permeated into the human body, the polymer was formed again, and the possibility of acting on the adiponectin receptors was confirmed (FIG. 8).

Example 9. Search for Overlapping of Sequence of Adiponectin Peptide with Other Proteins In the case of the adiponectin peptide prepared in the present invention, since the adiponectin peptide was a short amino acid sequence consisting of 5-mer, there is a possibility to actually overlap with amino acid sequences contained in other proteins existing in the human body. In this case, it is difficult to be shown as a sequence that specifically exists only in adiponectin, and thus, there is a problem that the possibility of acting specifically on the adiponectin receptors is low. Accordingly, a sequence that overlapped with the adiponectin peptide sequence was searched among all protein sequences existing in the human body using a UniProt database provided by NCBI in the United States.

As a result, in particular, in the case of the P5 peptide of the present invention, it was found that the P5 peptide existed only in a C1q complement protein superfamily to which the adiponectin protein belonged, and the P5 peptide was confirmed as a very specific peptide sequence for the adiponectin protein (FIG. 9).

Preparation Example 1. Preparation of Cosmetics

<1-1> Preparation of Skin Softener

A skin softener containing the adiponectin-derived peptide of the present invention as an active ingredient was prepared as shown in Table 2 below.

TABLE 2

| Raw material | Content (wt %) |
|---|---|
| Adiponectin-derived peptide of Example 1 | 10.00 |
| 1,3-butylene glycol | 1.00 |
| Disodium EDTA | 0.05 |
| Allantoin | 0.10 |
| Dipotassium glycyrrhizate | 0.05 |
| Citric acid | 0.01 |
| Sodium citrate | 0.02 |
| Glycereth-26 | 1.00 |
| Arbutin | 2.00 |
| Hydrogenated castor oil | 1.00 |
| Ethanol | 30.00 |
| Preservative | Trace |
| Coloring agent | Trace |
| Flavoring agent | Trace |
| Purified water | Residual |

<1-2> Preparation of Nourishing Cream

A nourishing cream containing the adiponectin-derived peptide of the present invention as an active ingredient was prepared as shown in Table 3 below.

TABLE 3

| Raw material | Content (wt %) |
|---|---|
| Adiponectin-derived peptide of Example 1 | 10.0 |

TABLE 3-continued

| Raw material | Content (wt %) |
|---|---|
| 1,3-butylene glycol | 7.0 |
| Glycerin | 1.0 |
| D-panthenol | 0.1 |
| Plant extract | 3.2 |
| Magnesium aluminum silicate | 0.3 |
| PEG-40 stearate | 1.2 |
| Stearic acid | 2.0 |
| Polysorbate 60 | 1.5 |
| Lipophilic glyceryl stearate | 2.0 |
| Sorbitan sesquioleate | 1.5 |
| Cetearyl alcohol | 3.0 |
| Mineral oil | 4.0 |
| Squalane | 3.8 |
| Carlylic/capric triglyceride | 2.8 |
| Vegetable oil | 1.8 |
| Dimethicone | 0.4 |
| Dipotassium glycyrrhizate | Trace |
| Allantoin | Trace |
| Sodium hyaluronate | Trace |
| Tocopheryl acetate | Suitable amount |
| Triethanol amine | Suitable amount |
| Preservative | Suitable amount |
| Flavoring agent | Suitable amount |
| Purified water | Residual |

<1-3> Preparation of Lotion

A lotion containing the adiponectin-derived peptide of the present invention as an active ingredient was prepared as shown in Table 4 below.

TABLE 4

| Raw material | Content (wt %) |
|---|---|
| Adiponectin-derived peptide of Example 1 | 3.5 |
| Cetostearyl alcohol | 1.6 |
| Stearate | 1.4 |
| Lipophilic glycerin monostearate | 1.8 |
| PEG-100 Stearate | 2.6 |
| Sorbitan sesquioleate | 0.6 |
| Squalene | 4.8 |
| Macadamia oil | 2 |
| Jojoba Oil | 2 |
| Tocopherol acetate | 0.4 |
| Methylpolysiloxane | 0.2 |
| Ethylparaben | 0.1 |
| Tocopherol acetate | 0.4 |
| Methylpolysiloxane | 0.2 |
| Ethylparaben | 0.1 |
| Propylparaben | 0.1 |
| 1,3-butylene glycol | 4 |
| Methylparaben | 0.1 |
| Xanthan gum | 0.1 |
| Glycerin | 4 |
| d-panthenol | 0.15 |
| Allantoin | 0.1 |
| Carbomer (2% aq. Sol) | 4 |
| Triethanol amine | 0.15 |
| Ethanol | 3 |
| pt 41891 | 0.1 |
| p-H20 | 48.3 |

<1-4> Preparation of Hair Tonic

A hair tonic having a composition shown in Table 5 below was prepared using the same method as a general preparation method of a hair tonic.

TABLE 5

| Raw material | Content (wt %) |
|---|---|
| Adiponectin-derived peptide of Example 1 | 5.0 |

TABLE 5-continued

| Raw material | Content (wt %) |
|---|---|
| Panthenol | 0.2 |
| Menthol | 0.3 |
| Salicylic acid | 0.25 |
| Sodium citrate | 0.65 |
| PEG-40 hydrogenated castor oil | 0.6 |
| $C_{12-14}$ Pareth-12 | 0.6 |
| Pigment | Suitable amount |
| Flavoring | Suitable amount |
| Ethanol | Suitable amount |
| Purified water | Residual |

<1-5> Preparation of Hair Shampoo

A hair shampoo having a composition shown in Table 6 below was prepared using the same method as a general preparation method of a hair shampoo.

TABLE 6

| Raw material | Content (wt %) |
|---|---|
| Adiponectin-derived peptide of Example 1 | 5.0 |
| Panthenol | 0.5 |
| Icotinic acid amide | 0.3 |
| Tocopheryl acetate | 0.1 |
| Biotin | 0.06 |
| Citric acid | 0.3 |
| Sodium lauryl sulfate solution (28%) | 40.0 |
| Disodium cocoamphodiacetate | 5.0 |
| Cocamidopropylbetaine | 3.0 |
| Cocamide DEA | 1.2 |
| Cetrimonium chloride | 1.0 |
| Dimethicone | 1.2 |
| Polyquaternium-10 | 0.5 |
| Triethanol amine | 0.55 |
| Glycerin | 0.5 |
| Carbomer | Suitable amount |
| Pigment | Suitable amount |
| Flavoring | Suitable amount |
| Ethanol | Suitable amount |
| Purified water | Residual |

<1-6> Preparation of Hair Conditioner

A hair conditioner having a composition shown in Table 7 below was prepared using the same method as a general preparation method of a hair conditioner.

TABLE 7

| Raw material | Content (wt %) |
|---|---|
| Adiponectin-derived peptide of Example 1 | 5.0 |
| Zinc pyrithione solution | 0.6 |
| Panthenol | 0.5 |
| Salicylic acid | 0.2 |
| Behentrimonium chloride | 5.0 |
| Cetyl alcohol | 3.0 |
| Cetostearyl alcohol | 2.0 |
| Isopropyl palmitate | 2.0 |
| Glycerin monostearate | 0.75 |
| PEG-100 stearate | 0.75 |
| Polysorbate | 0.5 |
| $C_{12-15}$ alkyl benzoate | 0.5 |
| Dimethicone | 3.0 |
| Copolymerized methylpolysiloxane | 0.5 |
| Hydroxyethylcellulose | 0.3 |
| Propylene glycol | 2.0 |
| Triethanol amine | Suitable amount |
| Pigment | Suitable amount |
| Flavoring | Suitable amount |

TABLE 7-continued

| Raw material | Content (wt %) |
|---|---|
| Phenoxyethanol | Suitable amount |
| Purified water | Residual |

Preparation Example 2. Preparation of Pharmaceutical Preparations

<2-1> Preparation of Powders

Adiponectin-derived peptide of the present invention . . . 2 g

Lactose . . . 1 g

The above ingredients were mixed and filled in an airtight bag to prepare powders.

<2-2> Preparation of Tablets

Adiponectin-derived peptide of the present invention . . . 100 mg

Corn starch . . . 100 mg

Lactose . . . 100 mg

Magnesium stearate . . . 2 mg

The above ingredients were mixed and then tableted according to a general tablet preparation method to prepare tablets.

<2-3> Preparation of Capsules

Adiponectin-derived peptide of the present invention . . . 100 mg

Corn starch . . . 100 mg

Lactose . . . 100 mg

Magnesium stearate . . . 2 mg

The above ingredients were mixed and then filled in gelatin capsules according to a general capsule preparation method to prepare capsules.

<2-4> Preparation of Pills

Adiponectin-derived peptide of the present invention . . . 1 g

Lactose . . . 1.5 g

Glycerin . . . 1 g

Xylitol . . . 0.5 g

The above ingredients were mixed and then prepared to be 4 g per 1 pill according to a general method.

<2-5> Preparation of Granules

Adiponectin-derived peptide of the present invention . . . 150 mg

Soybean extract . . . 50 mg

Glucose . . . 200 mg

Starch . . . 600 mg

The above ingredients were mixed and then added with 100 mg of 30% ethanol and dried at 60° C. to form granules and fill the granules in bags.

<2-6> Preparation of Injection Solution

Adiponectin-derived peptide of the present invention . . . 10 μg/ml

Diluted hydrochloric acid BP . . . until pH 3.5

Sodium chloride BP for injection . . . maximum 1 ml

The Adiponectin-derived peptide of the present invention was dissolved in an appropriate volume of sodium chloride BP for injection, the pH of the produced solution was adjusted to pH 3.5 with diluted hydrochloric acid BP, and then the volume was adjusted using sodium chloride BP for injection, and mixed thoroughly. The solution was filled in a 5 ml type I ampoule made of clear glass, the glass was dissolved, and sealed under an upper grid of air, and sterilized by autoclaving at 120° C. for 15 minutes or longer to prepare an injection solution.

The invention claimed is:

1. A cosmetic composition for promoting hair growth comprising one or more adiponectin-derived peptide selected from the group consisting of amino acid sequences of SEQ ID NOS: 16 to 21 as an active ingredient.

2. The cosmetic composition of claim 1, wherein the adiponectin-derived peptide is contained at a concentration of 0.001 mM to 20 mM.

3. The cosmetic composition of claim 1, wherein the cosmetic composition has any one formulation selected from the group consisting of a scalp treatment agent, a soap, a hair tonic, a shampoo, a rinse, a hair pack, a hair gel, a lotion, a conditioner, hair oil, mousse, a cream, a solid agent, a solution, an emulsion, a dispersant, a micelle, liposome, an ointment, a toner, an essence, a patch, and a spray.

* * * * *